United States Patent [19]
Crivello

[11] Patent Number: 6,031,014
[45] Date of Patent: Feb. 29, 2000

[54] INITIATOR COMPOSITIONS AND METHODS FOR THEIR SYNTHESIS AND USE

[76] Inventor: James V. Crivello, 756 Carlton Rd., Clifton Park, N.Y. 12065

[21] Appl. No.: 09/208,265

[22] Filed: Dec. 8, 1998

[51] Int. Cl.[7] .............................. C08G 59/68; C08F 2/00; C07D 339/08; C07D 335/08; C07C 331/00
[52] U.S. Cl. ................................ 522/31; 549/17; 549/27; 568/75; 568/18; 526/204
[58] Field of Search .......................... 568/18, 75; 522/25, 522/31; 549/17, 27; 526/204

[56] References Cited

U.S. PATENT DOCUMENTS

| | | | |
|---|---|---|---|
| 4,417,061 | 11/1983 | Crivello | 549/3 |
| 4,442,197 | 4/1984 | Crivello et al. | 430/280 |
| 5,047,568 | 9/1991 | Angelo et al. | 556/64 |

OTHER PUBLICATIONS

Böhme and Krause [*Chemische Berichte 82*, 426–432 (1949)], "über Dialkyl–phenacyl–sul–foniumsalze".

Flowers, Holt and Hope [*J. C. S. Perkin I* 1116–1120 (1973)] "Acid–induced Interaction of 2–Diazoacetophenones and Sulphides".

Crivello and Lam [*Journal of Polymer Science* 2877–2892 (1979)] "Photoinitiated Cationic Polymerization by Dialkylphenacylsulfonium Salts".

Crivello and Lam [*Journal of Polymer Science* 1021–1034 (1980)] "Photoinitiated Cationic Polymerization by Dialkyl–4–Hydroxyphenylsulfonium Salts".

Crivello and Lee [*Macromolecules 14* 1141–1147 (1981)] "Photosensitized Cationic Polymerizations Using Dialkylphenacylsulfonium".

Crivello [*Essex: Applied Science* p. 34, Allen, N.S. (Ed.) (1981)] "Developments in Polymer Photochemistry –2".

Crivello and Lee [*Macromolecules 16*, 864–870 (1983)] "Structural and Mechanistic Studies on the Photolysis of".

Crivello [*Cationic Polymerization and Related Process* 289–305 (1984)] "Recent Progress in the Design of".

Crivello [*Advances in Polymer Science 62*, 1–48 (1984)] "Cationic Polymerization—Iodonium and Sulfonium Salt Photoinitiators".

Toba et al, "Oxo–sulfonium complxes and their use as catalysts for photochemical and thermal polymerization of ethylenic compounds" CA:120–135389, 1994.

Ito et al, "Novel polymeric dissolution inhibitor for the design of sensitive, dry etch resistant, base–developable resisit", CA:110–182771, 1989.

*Primary Examiner*—Deborah C. Lambkin
*Attorney, Agent, or Firm*—Heslin & Rothenberg, P.C.

[57] ABSTRACT

Cationic polymerization initiators of formula

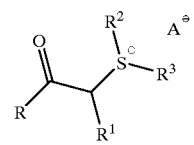

are disclosed. The acyl sulfonium salts of the present invention differ from known acyl sulfonium initiators in that the substituents $R^2$ and $R^3$ on the sulfur are larger and more complex than the lower alkyl and lower alkylene of known photoinitiators. Processes for the synthesis of the novel acyl sulfonium salts and prepolymer compositions containing them are also disclosed.

26 Claims, No Drawings

INITIATOR COMPOSITIONS AND METHODS FOR THEIR SYNTHESIS AND USE

FIELD OF THE INVENTION

The invention relates to initiators for cationic polymerization of reactive monomers.

BACKGROUND OF THE INVENTION

In recent years, there has been considerable interest in the photo-, e-beam and thermally induced cationic polymerization of many types of monomers and oligomers. Such polymerization systems are currently employed in a wide diversity of industrial applications including: non-stick release coatings, adhesives, abrasion resistant coatings for plastics, optical fiber coatings, reinforced composites and optical waveguides. Considerable future potential for growth of UV curable, cationically polymerizable systems exists because of the excellent properties of such coating systems, their low energy consumption and the lack of environmental pollution which derives from the elimination of the use of solvents.

Key to this technology was the development of highly photosensitive (i.e. high quantum yield) cationic photoinitiators which can be designed to be responsive to various UV wavelengths. Among the best photoinitiators which have been developed in recent years are diaryliodonium and triarylsulfonium salts of the structures I and II respectively, indicated below.

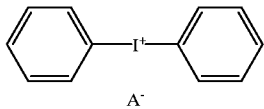

I

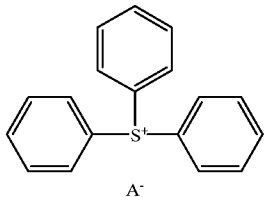

II

In photoinitiators I and II, $A^{\ominus}$ is a non-nucleophilic anion such as $CF_3SO_3^{\ominus}$, $ClO_4^{\ominus}$, $FSO_3^{\ominus}$, $SbF_6^{\ominus}$, $BF_4^{\ominus}$, $PF_6^{\ominus}$, $AsF_6^{\ominus}$, $(C_6F_5)_4B^{\ominus}$, $CB_{11}H_6Cl_6^{\ominus}$, and $CB_{11}H_6Br_6^{\ominus}$.

While I and II exhibit high quantum yields, they are only soluble in the most polar of cationically polymerizable monomers. Further, both of these photoinitiator classes are toxic. These two factors considerably limit both their attractiveness and their utility. In an effort to alleviate these problems, photoinitiators III and IV, bearing $C_{(1-20)}$ alkoxy groups, V, bearing two alkyl groups, and VI, bearing both an alkoxy and a hydroxy group, were developed.

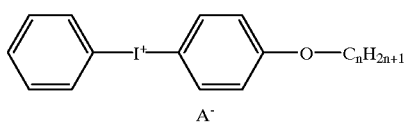

III

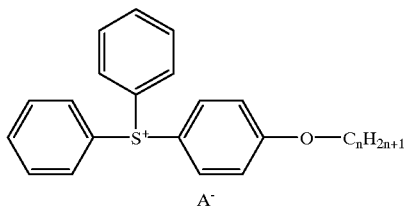

IV

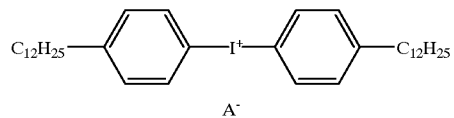

V

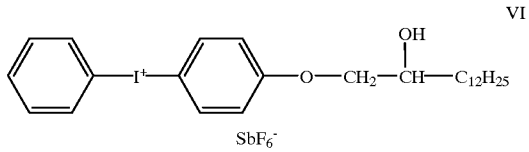

VI

These modifications were largely successful in rendering the respective salts non-toxic and soluble in a broader range of monomers.

An additional class of interesting photoinitiators, the dialkylphenacylsulfonium salts, having the general structure VII shown below, were described in the early 1980's:

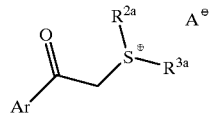

VII

In the compounds described, Ar was commonly phenyl, $R^{2a}$ was methyl and $R^{3a}$ was methyl, or $R^{2a}$ and $R^{3a}$ taken together formed a 5 or 6-membered ring. These compounds were useful cationic photoinitiators with certain classes of monomers, but they have never enjoyed the commercial success of the triarylsulfonium salts.

There remain considerable difficulties with the diaryliodonium and triarylsulfonium photoinitiators III–VI. While photoinitiators III–VI have better solubility characteristics as compared to I and II, they are still poorly soluble in non-polar monomers such as epoxidized hydrocarbon polymers, multifunctional vinyl, 1-propenyl and 1-butenyl ethers and in epoxy silicone oligomers employed for release coatings. Similarly, the dialkyl phenacylsulfonium photoinitiators VII generally display very poor solubility in these same monomers, as a result of which UV cure of the monomers and resins is considerably below optimum. Poor and erratic cure are observed in some cases and no cure in others. Moreover, in the case of those photoinitiators that are produced as a mixture of isomers, such as V, purification by conventional crystallization techniques is generally unsuccessful. As a result, formulations of these photoinitiators with reactive monomers and oligomers exhibit poor potlife, having a very pronounced tendency to undergo rapid and exothermic gelation on standing. This is highly undesirable. There is an unmet need for truly soluble, compatible, highly reactive, shelf-stable cationic photoinitiators. The instant invention satisfactorily resolves the problems outlined above with existing cationic photoinitiators.

SUMMARY OF THE INVENTION

In one aspect the invention relates to compounds of formula

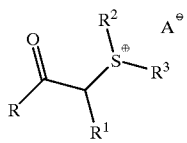

wherein: R is $C_6$ to $C_{20}$ alkyl, aryl, $C_6$ to $C_{20}$ substituted alkyl or substituted aryl; $R^1$ is hydrogen or $C_1$ to $C_8$ alkyl; $R^2$ is a $C_8$ to $C_{30}$ monovalent organic radical; $R^3$ is a $C_1$ to $C_{30}$ monovalent organic radical; and $A^\ominus$ is a non-nucleophilic anion. In this document, variables are defined when introduced and retain that definition throughout. In some embodiments $R^3$ may be a photosensitizing residue. $A^\ominus$ is usually $SbF_6^\ominus$, $BF_4^\ominus$, $PF_6^\ominus$, $AsF_6^\ominus$, or $(C_6F_5)_4B^\ominus$.

In another aspect, the invention relates to a method for synthesizing the foregoing compounds by (a) combining an α-haloketone of formula

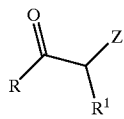

wherein Z is chlorine, bromine or iodine, with a sulfide of formula $R^2SR^3$ and a salt of formula $Y^\oplus A^\ominus$, wherein Y is an alkali or alkali metal, in a solvent in which the salt YZ is insoluble, (b) allowing reaction to progress to the formation of an insoluble salt YZ;

(c) separating the salt YZ from the remainder of the reaction mixture; and (d) isolating a compound of formula

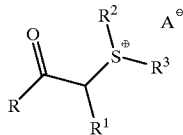

In another aspect, the invention relates to compositions for cationic polymerization comprising:

(a) a compound of formula

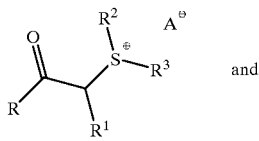 and (b) a polymerizable monomer or oligomer or mixture thereof.

These compositions may additionally include a film forming binder or a separate photosensitizer. The polymerizable monomer or oligomer may be: a mono- or polyfunctional epoxide, oxetane, lactone, cyclic acetal, spirocyclic ortho ester or carbonate, a silicone-modified epoxide, an epoxidized polybutadiene, an epoxidized polyisoprene, an epoxidized vegetable oil, an epoxidized alkene or terpene, a vinyl ether, 1-propenyl ether, 1-butenyl ether, or cyclic enol ether, a cyclic or acyclic ketene acetal, styrene, isoprene, isobutylene, an aziridine, or an oxazoline.

In another aspect, the invention relates to a method for forming a polymer comprising exposing the foregoing compositions to actinic radiation, heat, e-beam radiation or ionizing radiation.

In another aspect the invention relates to a polymeric composition that is the product of the polymerization of an epoxide monomer according to the method of the invention. These polymer products are characterized in that some portion of the polymeric chains have a terminus of the formula:

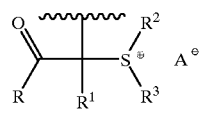

DETAILED DESCRIPTION OF THE INVENTION

The compositions of the present invention differ from those of the art in that the substituents $R^2$ and $R^3$ on the sulfur are larger and more complex than the lower alkyl and lower alkylene of known photoinitiators. The initiators of the invention are much more compatible with monomer mixtures and the resulting mixtures have much better pot lives and more advantageous physical properties for fabricating polymers than do those of the art. That such compounds have not been previously described is probably due to the fact that the processes used to make the compounds described in the art do not provide the compounds of the invention. Because the known reaction to produce phenacyl sulfonium salts is, in fact, an equilibrium process, it worked (in the sense of producing useable yields) only in those cases in which the phenacyl sulfonium bromide happened to crystallize from the reaction. Since this was a limited and special circumstance generally applicable only to the reaction of small, symmetrical sulfides, the acylsulfonium products from asymmetrical (i.e. $R^2 \neq R^3$) and "large" (i.e. the sum of $R^2+R^3>C_8$) sulfides have been previously unavailable. Thus the process of the present invention has provided, for the first time, the products that enjoy the advantages enumerated above.

Scheme I shows the method employed for the synthesis of dialkylphenacylsulfonium salts VII of the art.

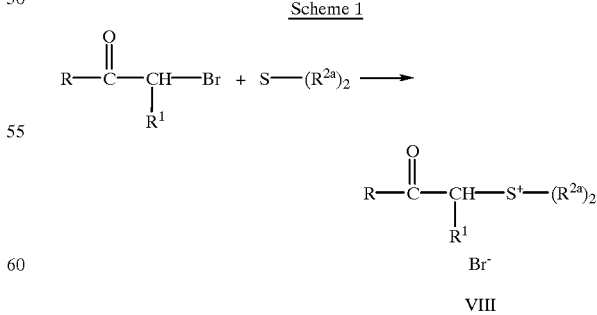

As shown, the α-bromo ketone was reacted with the dialkyl sulfide neat or in aqueous acetone to generate the sulfonium bromide VIII, which precipitated from solution. If a photoinitiator having a non-nucleophilic counterion was needed, the sulfonium bromide was dissolved in water and subjected to a metathesis reaction in a second step to give the desired photoinitiator, VII. While this method works well with low molecular weight or cyclic aliphatic sulfides, it either fails or gives very poor yields of the desired photoinitiators when high molecular weight sulfides having long alkyl groups are used. Unsymmetric sulfides, in which the two alkyl groups are different, fail entirely to undergo this sequence of reactions.

The initiators of the invention have the following general formula IX:

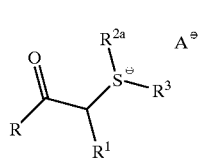

IX

In this formula, $R^2$ is a $C_8$ to $C_{30}$ monovalent organic radical, $R^3$ is a $C_1$ to $C_{30}$ monovalent organic radical; and $A^{\ominus}$ is a non-nucleophilic anion. Either one or both $R^2$ and $R^3$ may be linear, branched or cyclic alkyl groups or alkylaryl groups or groups containing unsaturated double or triple bonds. Further, either one or both $R^2$ and $R^3$ may contain hydroxyl (OH) groups. Preferred compounds are those in which R is aryl or substituted aryl; $R^1$ is hydrogen; $R^2$ is $C_{14}$ to $C_{30}$ alkyl, aryl, $C_{14}$ to $C_{30}$ substituted alkyl or substituted aryl and $R^3$ is $C_1$ to $C_{30}$ alkyl, aryl, $C_1$ to $C_{30}$ substituted alkyl or substituted aryl. Examples of preferred R groups are phenyl; indan-1-one-2-yl; α-tetralone-2-yl; biphenylyl; naphthyl; perylenyl, pyrenyl, anthracenyl, tetracenyl, coronenyl, benzoylphenyl, 9-oxothioxanthenyl; and phenyl substituted with halogen, nitro or alkoxy. Preferably $R^1$ is hydrogen. One set of preferred embodiments is the genus in which R is phenyl; $R^2$ is $C_8$ to $C_{30}$, preferably $C_{14}$ to $C_{30}$, alkyl and $R^3$ is lower alkyl. Alternatively, as discussed below, $R^3$ may be a photosensitizing residue. Preferred examples of $A^{\ominus}$ include $SbF_6^{\ominus}$, $BF_4^{\ominus}$, $PF_6^{\ominus}$, $AsF_6^{\ominus}$, and $(C_6F_5)_4B^{\ominus}$. The initiators of the invention are completely shelf-stable in monomer and oligomer compositions, and long pot-lives are observed.

These initiators are derived from the corresponding α-haloketones and the appropriate dialkyl sulfides by the direct one-step synthetic procedure of the invention. The initiators can be isolated and rigorously purified by conventional crystallization techniques. Alternatively, those initiators that are liquids may be readily purified by extraction techniques. Depicted in Scheme 2 is the method by which the new initiator compositions of this invention are produced.

Scheme 2

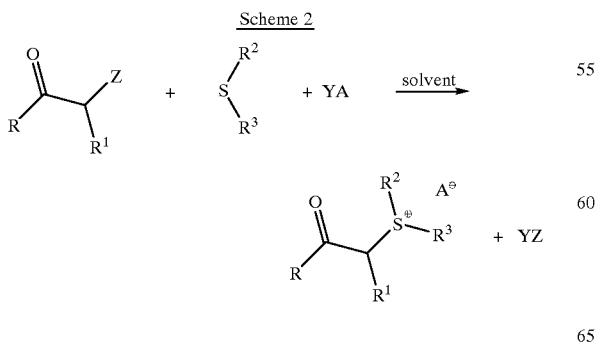

In Scheme 2, Z is either Cl Br or I and Y is typically an alkaline or alkaline earth metal (eg. Li, Na, K, Ca, Ba, Sr).

A variety of solvents may be employed, however, organic solvents and especially ketonic solvents such as acetone, methyl ethyl ketone, methyl isobutyl ketone, cyclohexanone, diisopropyl ketone, etc. have been found to be the most effective. An important consideration in choosing a solvent is that the salt YZ have a solubility in the chosen solvent at the volume of solvent employed such that a small percentage (usually less than 5%) of the salt that results from the reaction remains in solution. It will be appreciated that the functional definition of soluble, in the context of the invention, must account not merely for absolute solubility but also for volume. Thus a solvent in which the product is somewhat soluble could be used if the volume employed were small enough (i.e. the concentration high enough) to force the product out of solution. For example, if Y is sodium and Z is bromide, and the solubility of sodium bromide in solvent "S" is 1 g per liter, then, for a reaction that generates 20 g of sodium bromide, solvent "S" may be used in any amount less than one liter.

The reaction of the invention may be carried out at room temperature or at temperatures up to the boiling point of the solvent used.

This invention may be applied to a wide variety of dialkylphenacylsulfonium salts including those containing long alkyl groups and those bearing alkyl groups of differing chain lengths. Examples of these compounds are depicted below.

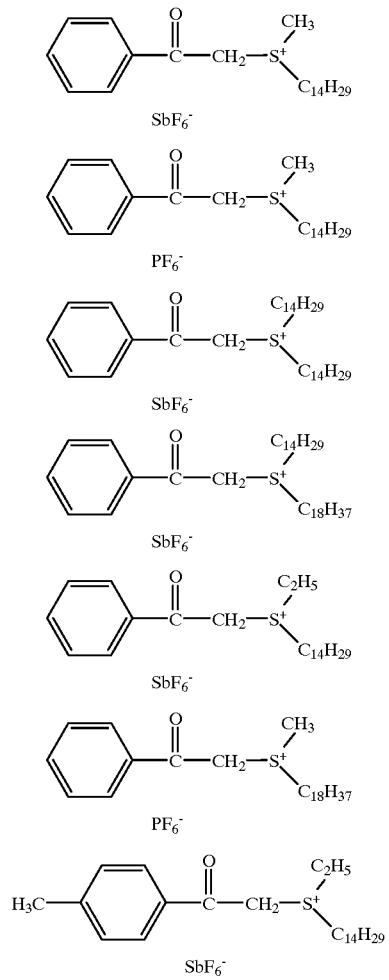

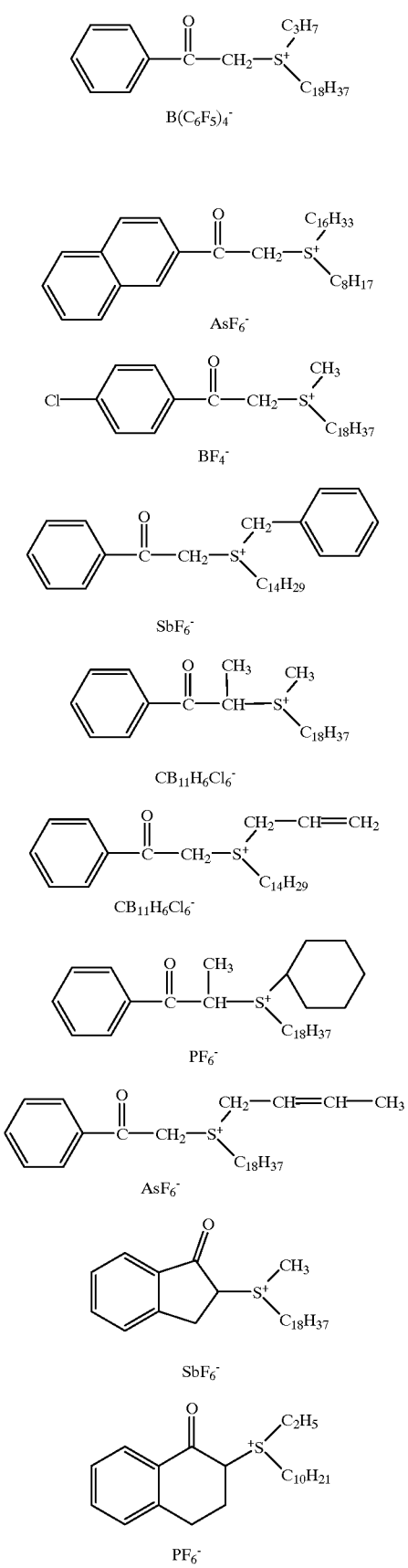

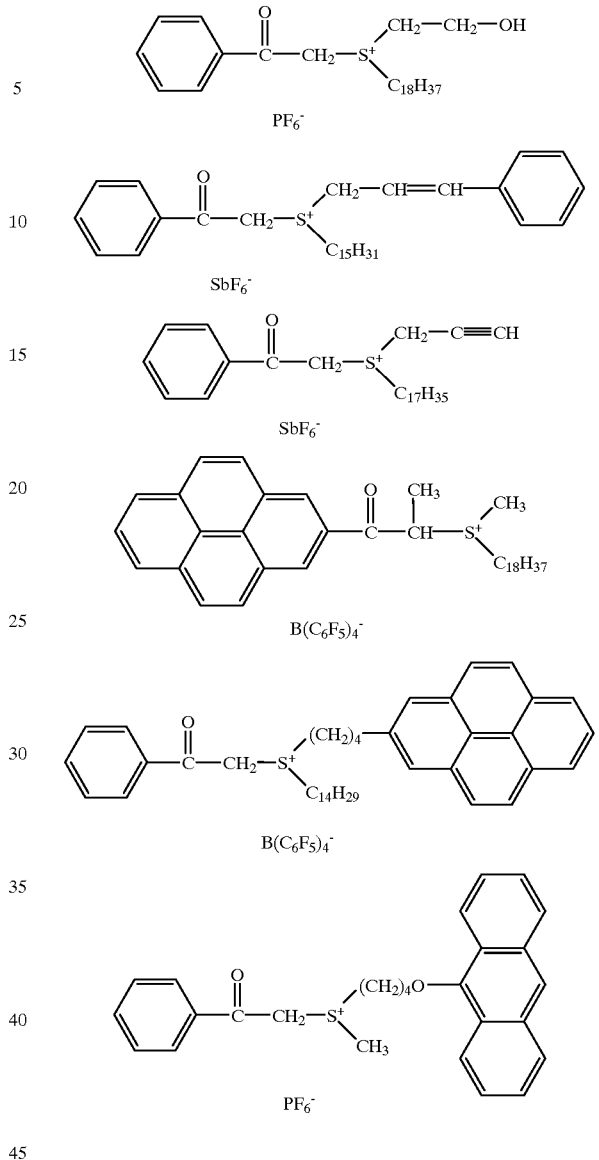

The initiators of this invention may be added to polymerizable monomers or oligomers in a solvent or directly as neat, solventless materials to catalyze the polymerization of a wide variety of cationically polymerizable monomer and oligomer systems. Monomers which may be employed together with the newly invented initiators include mono- and polyfunctional epoxides, oxetanes, lactones, cyclic acetals, spirocyclic orthoesters and carbonates, silicone-modified epoxides, epoxidized polybutadienes, epoxidized polyisoprenes, epoxidized vegetable oils, epoxidized alkenes and terpenes, vinyl ethers, 1-propenyl ethers, 1-butenyl ethers, cyclic enol ethers (eg. 2,3-dihydropyran, 2,3-dihydrofuran), cyclic and acyclic ketene acetals, styrene, isoprene, isobutylene, aziridines, oxazolines, and many others as well as combinations of the above monomers. Of particular interest in this invention is the use of the initiators to carry out the photopolymerization of epoxy functional silicones. For example, silicones bearing pendant epoxycyclohexyl functional groups, such as

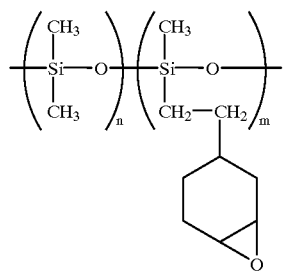

can be efficiently polymerized by irradiation with UV light using the above described photoinitiators. Photoinitiator-epoxysilicone compositions of the invention, such as the above, are used as UV curable release agents and are commonly applied to paper and plastics.

Another class of monomers and oligomers with which the initiators of this invention may be readily used are epoxidized olefins, for example, epoxidized butadiene, epoxidized isoprene, epoxidized styrene butadiene copolymers, epoxidized styrene isoprene copolymers, etc. Compositions containing the dialkylphenacylsulfonium salt and an epoxidized diene polymer or copolymer are especially attractive for use as UV curable pressure sensitive adhesives.

Still another class of non-polar monomers in which the initiators may find use are mono-, di- and multifunctional vinyl and 1-propenyl ethers. Typical examples of such compounds are as follows:

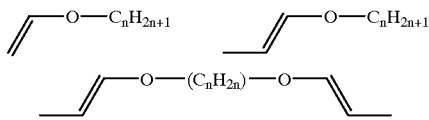

Where n=1–20. The initiators of this invention are readily soluble in these vinyl and 1-propenyl ether monomers.

An additional class of monomers comprises oxetanes and substituted oxetanes. Examples of such monomers are:

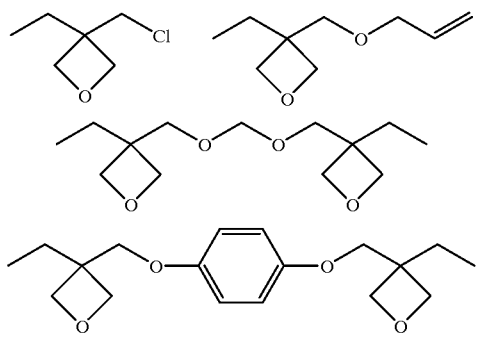

Irradiation of the monomer-initiator compositions in accordance with the practice of this invention can be achieved by the use of UV lamps such as mercury arc lamps (high, medium and low pressure), xenon arc lamps, high intensity halogen-tungsten arc lamps, microwave driven arc lamps and lasers. In the presence of photosensitizers, ambient sunlight may be used as a irradiation source. Additional means of irradiation which can be used are, for example, ionizing radiation using $^{60}Co$ γ-rays and electron-beam irradiation. Electron beam irradiation may be supplied using a low intensity source such as a linear cathode Electrocurtin instrument supplied by Energy Sciences, Inc. Willmington, Mass. or a high intensity source such as the 10 MeV instrument manufactured by the Atomic Energy Comission Ltd. of Canada.

In addition to the monomer and initiator components described above, the curable formulations may also include film forming binders such as polystyrene, poly-α-methylstryene, polyacenaphthalene, polyindene, polyphenols, polyimides and novolac resins. Inorganic fillers such as silica, talc, clay, calcium sulfate, hydrated alumina and glass, as well as carbon, polyolefin or polyimide fibers may be included to provide desirable mechanical characteristics. In general, processing aids in amounts up to 500 parts of filler per 100 parts of resin (i.e. initiator and monomer or oligomer) can be employed.

Many current users of cationic photopolymerization employ a combination of a cationic photopolymerization prepolymer mixture together with a free-radical polymerization prepolymer mix. The compositions of the present invention may be so employed. Thus, for example, an epoxide and an initiator of the invention may be combined with a multifunctional acrylate or methacrylate to provide a prepolymer mix that can be polymerized by cationic polymerization and free-radical polymerization sequentially or simultaneously.

The above materials may be further made sensitive to long wavelength UV and to visible light by the addition of external photosensitizers as described in U.S. Pat. No. 4,610,952. Among such photosensitizers are Michler's ketone, perylene, pyrene, anthracene, tetracene, coronene, stilbene, 1,4-diphenylbutadiene, 1,4-diphenylbutadiyne, 9-phenylanthracene, 9,10-diphenylanthracene, 9,10-diphenylethynylanthracene, 1,4-diethoxy-9-phenylanthracene, benzophenone, thioxanthone, 2-isopropylthioxanthone, 2-chlorothioxanthone, phenothiazine, and camphorquinone. In the course of their use in various applications, the novel initiator/resin compositions may be also combined with various particulate reinforcing agents, flow control and flatting agents, pigments and dyes and mold release agents.

Although as mentioned above, photosensitizers may be added to the initiator compositions of this invention to provide spectral broadening, it may be desirable to incorporate the functional elements of such photosensitizers into the initiator itself. A general formula of such a photoinitiator containing a photosensitizer group is:

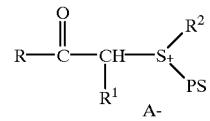

In this formula, R, $R^1$ and $R^2$ are as described previously; PS is a subset of $R^3$ in which the residue contains a photosensitizing group. Examples of such photosensitizing groups are for example:

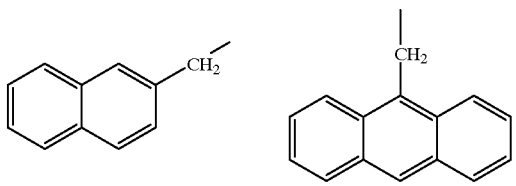

-continued

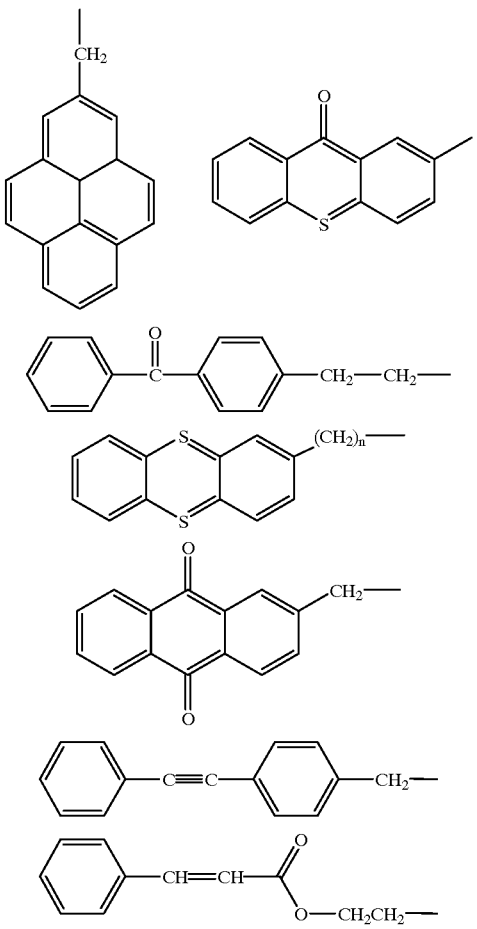

It has been found that heat curable compositions can also be provided by using a dialkylphenacylsulfonium salt initiator composition of this invention and a polymerizable monomer or oligomer. Suitable cationically polymerizable monomers and oligomers are as defined above. An effective amount of amount of the dialkylphenacylsulfonium salt initiator is an amount sufficient to provide at least 0.5% by weight of sulfur based on the weight of heat curable composition and preferably 1% to 10% based on the weight of the heat curable composition.

Typically, the initiators of this invention will be used as pure substances in the various applications for which they are intended. However, when convenience dictates, they may be dispensed as solutions in various carrier solvents. Among those solvents which may be used in accordance with this invention are: propylene carbonate, ethylene carbonate, γ-butyrolactone, ε-caprolactone, tricresylphosphate, anisole, xylene, cyclohexanone, diethylene glycol dimethyl ether, propylene glycol methyl ether acetate, butyl cellosolve, butyl acetate, amyl acetate, castor oil, diethylene glycol and many others.

The novel initiator compositions of the invention may be formulated with the above described monomers and oligomers to have many applications in addition to those described previously. For example, these formulations may be employed as protective and abrasion resistant coatings for wood, metals, plastics and glass. They may be employed as radiation curable adhesive or bonding agents. They may be employed and cured using lasers in the practice of stereolithography to generate solid, 3-dimensional objects. Combined with fibrous reinforcing agents they may be cured by UV, visible, $^{60}$Co γ-ray, and e-beam radiation to give high performance composites. They may be further used as radiation or thermally curable encapsulating and potting agents for electronic and microelectronic applications.

The terminology used herein is as follows:

A monovalent organic radical refers to any residue that can be covalently attached to a sulfur and subsequently reacted with an α-haloketone to produce an acyl sulfonium salt. Preferred $C_{14}$ to $C_{30}$ monovalent organic radicals and $C_1$ to $C_{30}$ monovalent organic radicals of the claimed invention include alkyl, alkenyl, and alkynyl residues, aryl residues, arylalkyl residues, and oxygenated derivatives thereof.

Alkyl is intended to include linear, branched, or cyclic hydrocarbon structures and combinations thereof. Lower alkyl refers to alkyl groups of from 1 to 4 carbon atoms. Examples of lower alkyl groups include methyl, ethyl, propyl, isopropyl, butyl, s-and t-butyl and the like. Preferred alkyl groups are those of $C_{30}$ or below. Cycloalkyl is a subset of alkyl and includes cyclic hydrocarbon groups of from 3 to 8 carbon atoms. Examples of cycloalkyl groups include c-propyl, c-butyl, c-pentyl, c-hexyl, norbornyl and the like.

Alkoxy or alkoxyl refers to groups of from 1 to 20 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through an carbonyl functionality. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered, partially or fully aromatic or heteroaromatic ring system containing 0–3 heteroatoms selected from O, N, or S; or a tricyclic 13- or 14-membered partially or fully aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 1 0-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl and aryl refer to alkyl and aryl wherein up to three H atoms in each residue are replaced with halogen, hydroxy, loweralkoxy, carboxy, carboalkoxy, oxy, carboxamido, cyano, $NO_2$, sulfoxide, sulfone, acylamino, amidino, phenyl, benzyl, heteroaryl, phenoxy, benzyloxy, or heteroaryloxy.

The following experimental procedures are included by way of example and are not intended to imply any limitation whatsoever.

Methyl Octadecylphenacylsulfonium Hexafluoroantimonate

Into a 100 mL round bottom flask equipped with a magnetic stirrer and a reflux condenser were placed 27.7 g (0.1 mol) 1-octadecylthiol, 21.3 g (0. 15 mol) methyl iodide, 11.2 g (0.2 mol) potassium hydroxide, 3.0 g tetra-n- butylammonium bromide and 20 mL toluene. The reaction mixture was heated to reflux for 1 hour and then cooled to room temperature. The reaction mixture was diluted with dichloromethane, placed in a separatory funnel and washed several times with distilled water to remove excess potassium hydroxide and potassium bromide. Next, the organic layer was placed on a rotary evaporator and the solvents and excess methyl iodide were removed. There remained methyl octadecyl sulfide as a white crystalline solid.

In a 100 mL Erlenmeyer flask were combined 10 g (0.05 mol) phenacyl bromide, 12.93 g (0.05 mol) sodium hexafluoroantimonate, 15 g (0.05 mol) methyl octadecyl sulfide and 40 mL methyl ethyl ketone (2-butanone). The reaction mixture was heated to boiling and maintained at this temperature for 30 minutes. During this time, sodium bromide was observed to precipitate. The reaction mixture was filtered to remove the inorganic salts and the resulting solution placed on a rotary evaporator to remove solvents. The product crystallized to give the desired salt, m.p. 80–82° C. Recrystallization from isopropanol gave a very light tan salt with a melting point of 79–80° C.

$^1$H NMR (CDCl$_3$) δ(ppm) 7.50 ($H_b$, 2H); 7.67 ($H_c$, 1H); 7.98 ($H_a$, 2H); 3.45 ($H_e$, 2H); 5.10 ($H_d$, 2H); 2.97 ($H_h$, 3H); 1.1–1.9 ($H_f$, 32H); 0.87($H_g$, 3H); Elemental Analysis: Calcd. for $C_{27}H_{47}OSSbF_6$; C, 49.48%; H, 7.23%. Found: C, 49.8%; H, 7.26%. Molecular Mass: 655.50 g/mol.

When an attempt was made to prepare this initiator using the procedure of Böhme and Krause [*Chemische Berichte* 82, 426–432 (1949)], no sulfonium salt initiator could be isolated.

A 1% solution of the above sulfonium salt initiator was prepared in 3,4-epoxycyclohexylmethyl 3',4'-epoxycyclohexane carboxylate. Irradiation of this mixture as a 1 mil film on a glass plate using a GE H3T7 medium pressure mercury arc lamp at a distance of 10 cm produced a tack-free film after a 5 second exposure. Similarly, a 1% solution of the sulfonium salt initiator in bis-1,3(3,4-epoxycyclohexylethyl)-1,1,3,3-tetramethyldisiloxane gave a tack-free film after a 2 second irradiation. Further, a 1% solution of the above described sulfonium salt initiator dissolved in the epoxy silicone paper release resin UV-9315 (supplied by General Electric Silicones) gave a tack-free film after a 2 second irradiation.

A 2% solution of the sulfonium salt initiator in bis-1,3(3,4-epoxycyclohexylethyl)-1,1,3,3-tetramethyldisiloxane was spread as a 1 mil film using a wire-wound drawbar onto a bare 7 mil aluminum sheet. The substrate was exposed at a rate of 50 feet per minute to a 4 Mrad e-beam (RPC Instruments). The monomer underwent full cure to a solid, tack-free film under these conditions. The cured film was insoluble in all common solvents, indicating that it was crosslinked.

In further tests, a 1% by weight solution of the above initiator in epoxidized soybean oil was prepared by simply dissolving the solid initiator in the liquid monomer at room temperature. The solubility was excellent. Irradiation as described above for five seconds resulted in a cured film. The initiator is similarly soluble in an epoxidized isoprene-styrene block copolymer (Shell EKP 207). Irradiation of a 1% solution of this photoinitiator in the liquid copolymer for three seconds resulted in a clear, flexible film. Similarly, the initiator was readily dissolved in low molecular weight epoxidized poly(1,2-butadiene) (Viking Chemical Co.). A tack-free flexible film was formed after an irradiation period of three seconds. In all the above cases, the solubility of conventional cationic photoinitiators in the monomer is very low and for that reason, photopolymerization of the resulting compositions is highly inefficient.

Methyl Octylphenacylsulfonium Hexafluoroantimonate

Into a 100 mL round bottom flask equipped with a magnetic stirrer and reflux condenser were placed 16.0 g (0.1 mol) methyl octyl sulfide (obtained from the Aldrich Chemical Co.), 19.9 g (0.1 mol) phenacyl bromide, 25.87 g (0.1 mol) sodium hexafluoroantimonate and 40 mL acetone. The reaction mixture was brought to reflux and held at this temperature for 15 minutes. The mixture was filtered through a plug of glass wool (to remove the sodium bromide which was formed during the reaction) and the solvent was removed on a rotary evaporator, leaving 43.1 g (83.6% yield) of the desired methyl octylphenacylsulfonium hexafluoroantimonate as a tan colored solid. The product was further purified by recrystallization, first from a 1:3 mixture of water and ethanol, then, isopropanol. The pure, colorless, crystalline initiator had a melting point of 75–76° C. The initiator was soluble in a wide variety of common solvents such as acetone, methyl ethyl ketone, chloroform and methylene chloride.

$^1$H NMR (CDCl$_3$) δ(ppm) 7.26 ($H_b$, 2H); 7.63 ($H_c$, 1H); 7.95 ($H_a$, 2H); 3.34 ($H_e$, 2H); 5.05 ($H_d$, 2H); 2.93 ($H_h$, 3H), 1.2–1.85 ($H_f$, 12H); 0.86 ($H_g$, 3H). Elemental Analysis: Calcd, for $C_{17}H_{27}OSSbF_6$: C, 39.63%; H, 5.28%. Found: C, 39.72%; H, 5.28%. Molecular Mass 515.2 g/mol., m.p.= 75–76° C.

The above initiator was dissolved as a 1% solution in 3,4-epoxycyclohexylmethyl 3',4'-epoxycyclohexanecarboxylate and irradiated as a 1 mil film using a 200 Watt GE H3T7 medium pressure mercury arc lamp. The irradiation time to produce a tack-free film was 2 seconds.

Similarly prepared were:

Methyl Hexadecylphenacylsulfonium Hexafluoroantimonate

Elemental Analysis: Calcd. For $C_{25}H_{43}OSSbF_6$: C, 47.86%; H, 6.91%. Found: C, 48.00%; H, 7.00%. Molecular Mass: 627.42 g/mol., m.p.=74–75.5 ° C.

Methyl Tetradecylphenacylsulfonium Hexafluoroantimonate

Elemental Analysis: Calcd. For $C_{23}H_{39}OSSbF_6$: C, 46.09%; H, 6.56%. Found: C, 46.33%; H, 6.63%. Molecular Mass: 599.36 g/mol., m.p.=65–66.5° C.

Methyl Dodecylphenacylsulfonium Hexafluoroantimonate

Elemental Analysis: Calcd. For $C_{21}H_{35}OSSbF_6$: C, 44.15%; H, 6.17%. Found: C, 44.31%; H, 6.22%. Molecular Mass: 571.31 g/mol., m.p.=58.5–60° C.

Ethyl Octadecylphenacylsulfonium Hexafluoroantimonate

Elemental Analysis: Calcd. For $C_{28}H_{49}OSSbF_6$: C, 50.23%; H, 7.38%. Found: C, 46.33%; H, 6.63%. Molecular Mass: 669.50 g/mol., m.p.=70–70.5° C.

Many of the α-haloketones and sulfides that are employed in the process of the invention are commercially available. Those α-haloketones that are not commercially available are readily synthesized from the corresponding ketones by free-radical halogenation using methods well known in the art. Similarly, those long-chain and asymmetric sulfides that are not commercially available are synthesized from the corresponding mercaptan and an alkylating agent (such as an alkyl halide), as described above for methyl octadecyl sulfide.

I claim:
1. A compound of formula

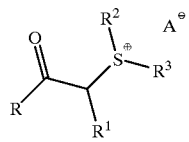

wherein:
R is $C_6$ to $C_{20}$ alkyl, aryl, $C_6$ to $C_{20}$ substituted alkyl or substituted aryl;
$R^1$ is hydrogen or $C_1$ to $C_8$ alkyl;
$R^2$ is a $C_8$ to $C_{30}$ alkyl, alkenyl, alkynyl, aryl, arylalkyl residue or oxygenated derivative thereof;
$R^3$ is a $C_1$ to $C_{30}$ alkyl, alkenyl, alkynyl, aryl, arylalkyl residue or oxygenated derivative thereof;
$A^\ominus$ is a non-nucleophilic anion; and
$R^2$ is different from $R^3$.

2. A compound according to claim 1 wherein R is aryl or substituted aryl.

3. A compound according to claim 1 wherein $R^1$ is hydrogen.

4. A compound according to claim 1 wherein $R^2$ is $C_8$ to $C_{30}$ alkyl, aryl, $C_8$ to $C_{30}$ substituted alkyl or substituted aryl and $R^3$ is $C_1$ to $C_{30}$ alkyl, aryl, $C_1$ to $C_{30}$ substituted alkyl or substituted aryl.

5. A compound according to claim 4 wherein
R is chosen from phenyl; biphenylyl; naphthyl; perylenyl, pyrenyl, anthracenyl, tetracenyl, coronenyl, benzoylphenyl, 9-oxothioxanthenyl; and phenyl substituted with halogen, nitro or alkoxy; and
$R^1$ is hydrogen.

6. A compound according to claim 5 wherein $R^3$ is lower alkyl.

7. A compound according to claim 6 wherein R is phenyl and $R^2$ is $C_{14}$ to $C_{30}$ alkyl.

8. A compound according to claim 5 wherein $R^3$ is chosen from

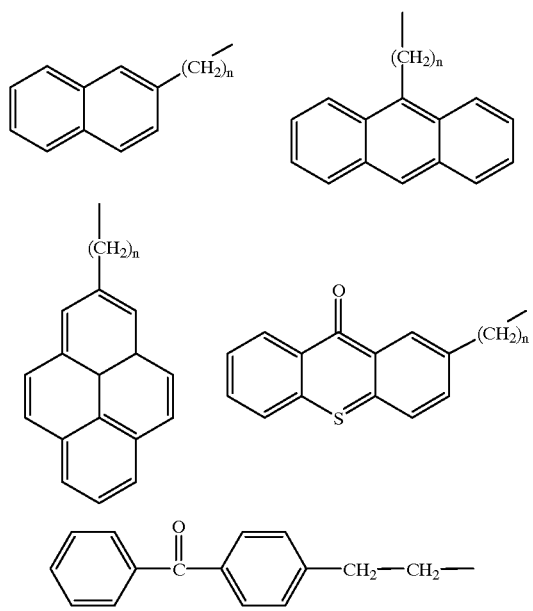

-continued

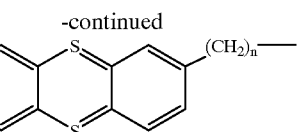

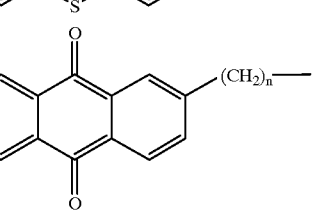

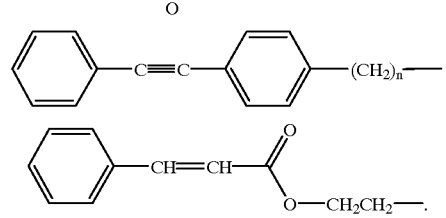

9. A compound according to claim 1 wherein $A^\ominus$ is chosen from $SbF_6^\ominus$, $BF_4^\ominus$, $PF_6^\ominus$, $AsF_6^\ominus$, and $(C_6F_5)_4B^\ominus$.

10. A method for preparing a compound of formula

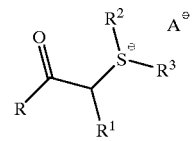

wherein:
R is $C_6$ to $C_{20}$ alkyl, aryl, $C_6$ to $C_{20}$ substituted alkyl or substituted aryl; $R^1$ is hydrogen or $C_1$ to $C_8$ alkyl; $R^2$ is a $C_8$ to $C_{30}$ alkyl alkenyl, alkynyl, aryl, arylalkyl residue or oxygenated derivative thereof; $R^3$ is a $C_1$ to $C_{30}$ alkyl, alkenyl, alkynyl, aryl, arylalkyl residue or oxygenated derivative thereof; and
$A^\ominus$ is a non-nucleophilic anion, comprising the steps of:
 (a) combining an α-haloketone of formula

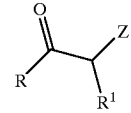

wherein Z is chlorine, bromine or iodine, with a sulfide of formula $R^2SR^3$ and a salt of formula $Y^\oplus A^\ominus$, wherein Y is an alkali or alkaline earth metal, in a solvent in which the salt YZ is insoluble;
 (b) allowing reaction to progress to the formation of an insoluble salt YZ;
 (c) separating said salt YZ from the remainder of the reaction mixture; and
 (d) isolating said compound of formula

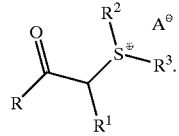

11. A method according to claim 10 wherein R is aryl or substituted aryl and $R^1$ is hydrogen.

12. A method according to claim 10 wherein $R^2$ is $C_8$ to $C_{30}$ alkyl, aryl, $C_8$ to $C_{30}$ substituted alkyl or substituted aryl and $R^3$ is $C_1$ to $C_{30}$ alkyl, aryl, $C_1$ to $C_{30}$ substituted alkyl or substituted aryl.

13. A method according to claim 12 wherein R is phenyl; $R^2$ is $C_8$ to $C_{30}$ alkyl; and $R^3$ is lower alkyl.

14. A method according to claim 10 wherein $A^\ominus$ is chosen from $SbF_6^\ominus$, $BF_4^\ominus$, $PF_6^\ominus$, and $(C_6F_5)_4B^\ominus$ and Y is chosen from sodium, potassium, lithium, barium, calcium and strontium.

15. A method according to claim 10 wherein said solvent is a ketonic solvent.

16. A composition for cationic polymerization comprising:

(a) a compound of formula

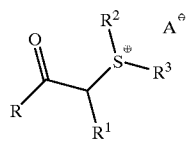

wherein:

R is $C_6$ to $C_{20}$ alkyl, aryl, $C_6$ to $C_{20}$ substituted alkyl or substituted aryl; $R^1$ is hydrogen or $C_1$ to $C_8$ alkyl; $R^2$ is a $C_8$ to $C_{30}$ alkyl, alkenyl, alkynyl, aryl, arylalkyl residue or oxygenated derivative thereof; $R^3$ is a $C_1$ to $C_{30}$ alkyl, alkenyl, alkynyl, aryl, arylalkyl residue or oxygenated derivative thereof; $A^\ominus$ is a non-nucleophilic anion; and $R^2$ is different from $R^3$; and (b) a polymerizable monomer or oligomer or mixture thereof.

17. A composition according to claim 16 wherein R is aryl or substituted aryl and $R^1$ is hydrogen.

18. A composition according to claim 16 wherein $R^2$ is $C_8$ to $C_{30}$ alkyl, aryl, $C_{14}$ to $C_{30}$ substituted alkyl or substituted aryl and $R^3$ is $C_1$ to $C_{30}$ alkyl, aryl, $C_1$ to $C_{30}$ substituted alkyl or substituted aryl.

19. A composition according to claim 16 wherein R is phenyl; $R^2$ is $C_8$ to $C_{30}$ alkyl; and $R^3$ is lower alkyl.

20. A composition according to claim 16 wherein $A^\ominus$ is chosen from $SbF_6^\ominus$, $BF_4^\ominus$, $PF_6^\ominus$, $AsF_6^\ominus$, and $(C_6F_5)_4B^\ominus$ and Y is chosen from sodium, potassium, lithium, barium, calcium and strontium.

21. A composition according to claim 16 additionally comprising a film forming binder.

22. A composition according to claim 16 additionally comprising a photosensitizer.

23. A composition according to claim 16 wherein said polymerizable monomer or oligomer is chosen from: mono- and polyfunctional epoxides, oxetanes, lactones, cyclic acetals, spirocyclic ortho esters and carbonates, epoxy-modified silicones, epoxidized polybutadienes, epoxidized polyisoprenes, epoxidized vegetable oils, epoxidized alkenes and terpenes, vinyl ethers, 1-propenyl ethers, 1-butenyl ethers, cyclic enol ethers, cyclic and acyclic ketene acetals, styrene, isoprene, isobutylene, aziridines, and oxazolines.

24. A composition according to claim 23 wherein said polymerizable monomer or oligomer is chosen from: mono- and polyfunctional epoxides, oxetanes, epoxy-modified silicones, epoxidized polybutadienes, epoxidized polyisoprenes, epoxidized vegetable oils, epoxidized alkenes and terpenes, vinyl ethers, 1-propenyl ethers and 1-butenyl ethers.

25. A method for forming a polymer comprising exposing a composition according to claim 16 to actinic radiation, heat, e-beam radiation or ionizing radiation.

26. A polymeric composition comprising a polymer having oxyalkylene repeating units and a terminus of the formula:

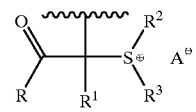

wherein:

R is $C_6$ to $C_{20}$ alkyl; aryl, $C_6$ to $C_{20}$ substituted alkyl or substituted aryl;

$R^1$ is hydrogen or $C_1$ to $C_8$ alkyl;

$R^2$ is a $C_8$ to $C_{30}$ alkyl, alkenyl, alkynyl, aryl, arylalkyl residue or oxygenated derivative thereof;

$R^3$ is a $C_1$ to $C_{30}$ alkyl, alkenyl, alkynyl, aryl, arylalkyl residue or oxygenated derivative thereof;

$A^\ominus$ is a non-nucleophilic anion; and $R^2$ s different from $R^3$.

* * * * *

UNITED STATES PATENT AND TRADEMARK OFFICE
CERTIFICATE OF CORRECTION

PATENT NO.   : 6,031,014
DATED        : February 29, 2000
INVENTOR(S)  : Crivello It is certified that error appears in the above-identified patent and that said Letters Patent is hereby corrected as shown below:

Please delete the structure at Column 10, line 60 to Column 11, line 37

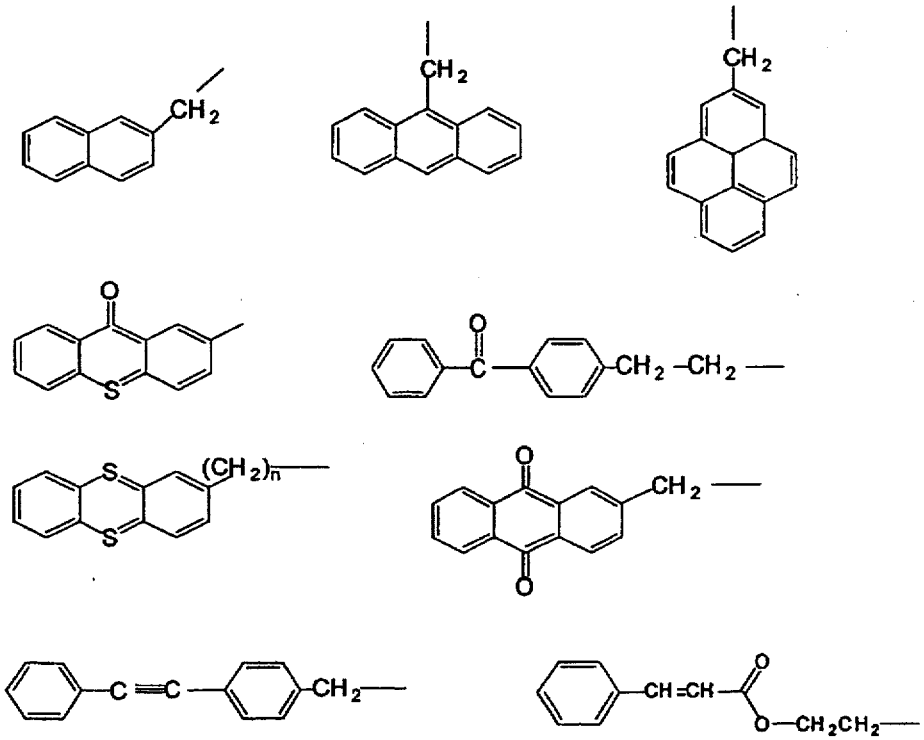

UNITED STATES PATENT AND TRADEMARK OFFICE
CERTIFICATE OF CORRECTION

PATENT NO. : 6,031,014
DATED : February 29, 2000
INVENTOR(S) : Crivello

Page 2 of 2

It is certified that error appears in the above-identified patent and that said Letters Patent is hereby corrected as shown below:

and replace with:

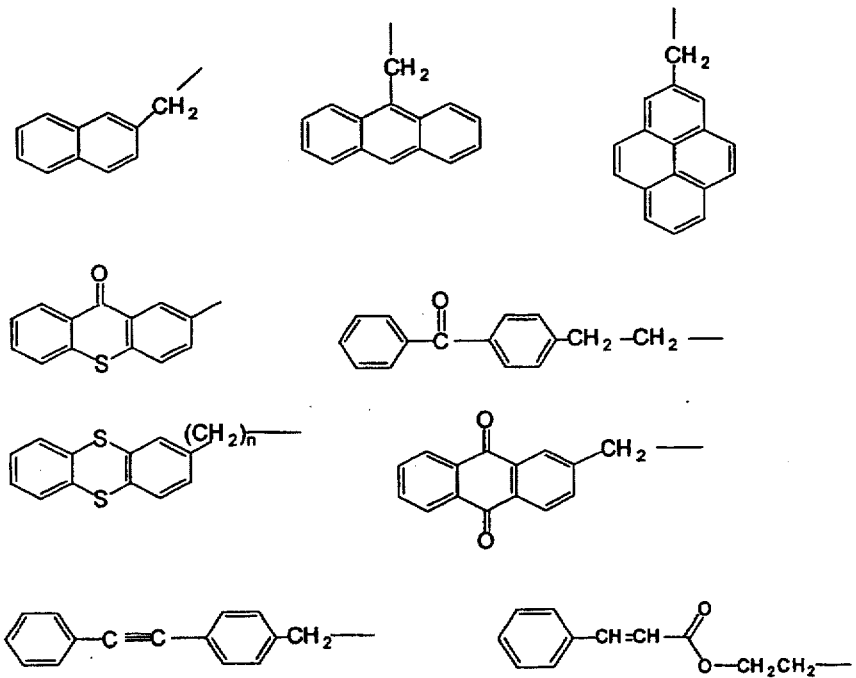

Signed and Sealed this

Eleventh Day of December, 2001

Attest:

NICHOLAS P. GODICI
Attesting Officer    Acting Director of the United States Patent and Trademark Office